United States Patent [19]

Rohrbach

[11] 4,268,419

[45] May 19, 1981

[54] SUPPORT MATRICES FOR IMMOBILIZED ENZYMES

[75] Inventor: Ronald P. Rohrbach, Forest Lake, Ill.

[73] Assignee: UOP Inc., Des Plaines, Ill.

[21] Appl. No.: 95,020

[22] Filed: Nov. 16, 1979

[51] Int. Cl.³ .................... B01J 31/06; C12N 11/08; C12N 11/14

[52] U.S. Cl. .................................. 252/430; 435/176; 435/180

[58] Field of Search ................ 252/430; 435/180–182, 435/174–177; 260/6

[56] References Cited

U.S. PATENT DOCUMENTS

| | | | |
|---|---|---|---|
| 4,066,504 | 1/1978 | Krasnobajew et al. | 528/246 |
| 4,141,857 | 2/1979 | Levy et al. | 252/430 |
| 4,184,986 | 1/1980 | Krasnobajew et al. | 260/6 |

*Primary Examiner*—P. E. Konopka
*Attorney, Agent, or Firm*—James R. Hoatson, Jr.; Raymond H. Nelson; William H. Page, II

[57] ABSTRACT

An improved method of preparing support matrices for immobilization of reactive chemical entities, such as enzymes, comprises deposition of a polyamine on core support, such as an inorganic oxide, contacting the polyamine-coated core support with a bifunctional reagent which cross-links the polyamine and provides pendant functional groups, and recovering the matrix, wherein the improvement comprises means of depositing the polyamine as a thin, uniform film.

3 Claims, 1 Drawing Figure

Immobilized Enzyme System

Immobilized Enzyme System
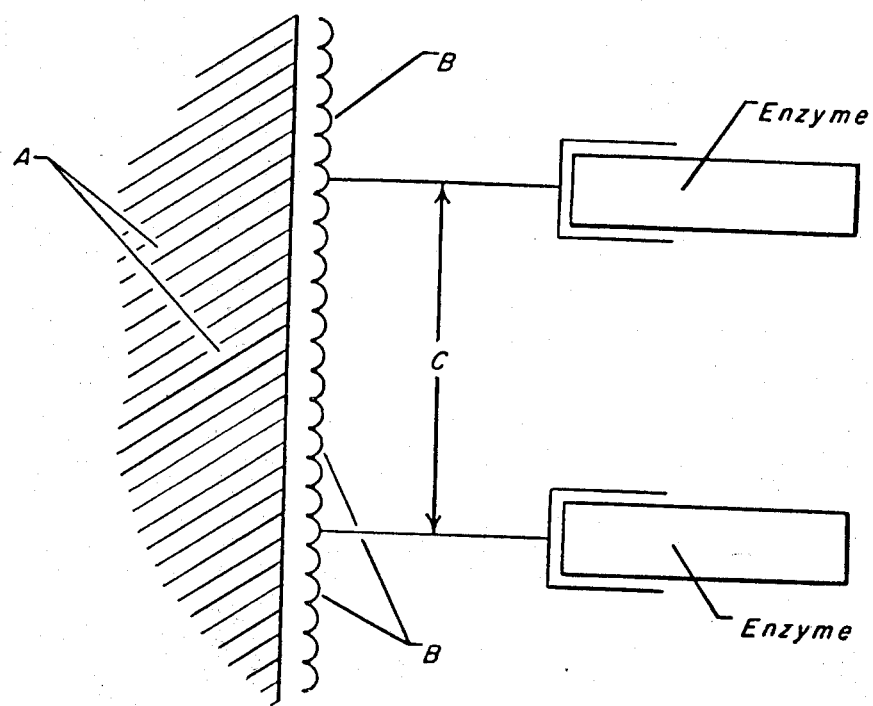

SUPPORT MATRICES FOR IMMOBILIZED ENZYMES

BACKGROUND OF THE INVENTION

Enzyme-catalyzed reactions often have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzyme for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in Levy and Fusee, U.S. Pat. No. 4,141,857, where a polyamine is absorbed on a metal oxide such as alumina, treated with an excess of a bifunctional reagent, such as glutaraldehyde, so as to cross-link the amine, and then contacting the mass with enzyme to form covalent bonds between the pendant aldehyde groups and an amino group on the enzyme. The support matrix prepared according to the aforementioned invention has great utility in immobilizing reactive chemical entities. Enzymes are but one class of such reactive chemical entities.

It is highly desirable that immobilized enzyme systems, i.e., the structure which results from binding of an enzyme to a support matrix, be prepared reproducibly and with maximum enzyme activity. Reproducibility and maximization of enzymatic activity is paramount for technological efficiency and commercial success.

SUMMARY OF THE INVENTION

An object of this invention is to provide an improved method of preparing a support matrix used to immobilize reactive chemical entities comprising treating an inorganic solid support with a polyamine, subsequently cross-linking said polyamide with a bifunctional reagent, and recovering the resulting support matrix, wherein the improvement comprises drying the matrix, before contacting with said bifunctional reagent, to more evenly distribute the polyamine on the surface of the solid inorganic support. In one embodiment said inorganic solid support is alumina, said polyamide is polyethyleneimine, said bifunctional reagent is glutaraldehyde, and the structure is dried prior to treatment with glutaraldehyde. Other embodiments and objects will be recognized from the description therein.

DESCRIPTION OF THE FIGURE

Many immobilized enzyme systems, such as that described above, have a common conceptual basis which is depicted pictorially in the FIGURE. It is to be understood that enzymes are merely one class of reactive chemical entities which may be immobilized and subsequently utilized in a chemical process.

There is a central core support, A, whose primary purpose is to provide mechanical and thermal stability to the system and which is chemically inert in the enzymatic reaction. The intermediate bonding layer, B, provides an interface between the core and the pendant groups, C. This layer may be held to the core either by physical entrapment, as within the pores of A, by strong short-range physical and/or chemical forces, as by surface adsorption or absorption, by chemical binding to the surface of the core support, or by a combination of the above. The pendant groups, C, may be part of the molecular structure of the binding layer, or may be chemically bonded to a suitable site on the binding layer. Such pendant groups are characterized by the presence of a chemically reactive functionality, usually terminally situated, which can covalently bond to some part of the enzyme, or other reactive chemical entity, sufficiently removed from its "active site" so as not to interfere substantially with its catalytic activity.

DESCRIPTION OF THE INVENTION

This invention relates to an improved method of preparing the structure depicted in the FIGURE and to the resulting improved structure itself. The central core support, A in the FIGURE, may be a metal oxide, preferably alumina and silica, glass, a ceramic or a metal. It needs to provide structural integrity, especially mechanical strength, have good characteristics in a system where there is a liquid flow, and provide a surface, wholly or in part, to which a layer of organic material can be attached either by physical or chemical means, or by a combination of them.

The binding layer, B, may be an organic polymer or a resin. Examples of such binding layers include functionalized polyethylenes, polyamines cross-linked with agents such as dialdehydes and diisocyanates, and others known to those skilled in the art. In a preferred embodiment the binding layer is a polyamine, such as polyethyleneimine, tetraethylenepentamine, ethylenediamine, diethylenetriamine, triethylenetetramine, pentaethylenehexamine, hexamethylenediamine, phenylenediamine, and the like, cross-linked via a reagent selected from the group consisting of dialdehydes and diisocyanates, as for example glutaraldehyde, succindialdehyde, toluenediisocyanate, and the like. In another preferred embodiment the binding layer is a functionalized polystyrene, such as aminopolystyrene, cross-linked by one of the aforementioned agents.

The pendant group, C, may be an independently functionalized group of the polymer, as for example an aldehydic moiety attached via mediating carbon atoms to a polyethylene chain, an independently functionalized group of a resin, or an unreacted terminus of the cross-linking agent wherein the other terminus is covalently bonded to the binding layer. In a preferred embodiment the pendant group arises from a cross-linking agent selected from the group consisting of dialdehydes and diisocyanates.

In some instances the demarcation between core support, A, binding layer, B, and pendant group, C, may seem indistinct. For example, the binding layer may appear to be part of the core, and might even contain a functional group which can covalently bond to an enzyme, thereby providing an immobilized enzyme system. A representative of this class is a chemically modified glass whose surface bears an organic residue having a functional group capable of covalently bonding to an enzyme. This invention relates to such a system, and to all systems which are functionally equivalent to, or can be functionally described by the representation in the FIGURE, however that may be attained in any specific immobilized enzyme system. The combination of the structures, A, B, and C forms a support matrix; addition of enzyme forms an immobilized enzyme system.

The improvement in the method of preparing a support matrix taught herein may be applied to any immobilized reactive chemical entity in which the reactive molecule can react with the pendant functional group without substantial loss of chemical activity. Enzymes form an important class of such reactive molecules, examples of which include glucose isomerase, glucoamylase, lactase, cellulase, glucose oxidase, perioxidase, ribonuclease, urease, histidase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, deoxyribonuclease, etc. It is to be understood that these enzymes are cited solely for illustrative purposes and it is not to be construed as a limitation of this invention. Other enzymes may be utilized, but not necessarily with equivalent results.

The Levy and Fusee U.S. Pat. No. 4,141,857, teaches the preparation of a class of support matrices corresponding to the description above. The process of the aforementioned invention is simple and conveniently performed, either in batch or continuous mode, at both a laboratory and commercial scale. For example, an inorganic oxide, such as gamma alumina, may be contacted with an aqueous solution of a polyamine, such as polyethyleneimine, where the polyamine is present at a concentration from about 1% to about 50%. Excess liquid is removed by suitable means, as by decantation, and the oxide is washed with water to remove excess polyamine. An aqueous solution of cross-linking agent, such as glutaraldehyde, containing from about 1% to 25% of the bifunctional reagent is added in an amount sufficient to provide an excess of from about 3 to about 50 or more moles of said bifunctional reagent per mole of polyamine. This solution is contacted, with occasional mixing, with the polyamine-coated oxide for a time sufficient to ensure equilibrium, generally from about 5 minutes to about 5 hours. Liquid is then removed from the oxide support by suitable means, such as by decantation, and the solid support is washed well with water to remove adhering, but not chemically bound, bifunctional reagent. At this stage the preparation of the support matrix is complete; the support matrix is ready to immobilize reactive chemical entities by covalently bonding them at a suitable site. For example, the matrix may be contacted, with mixing, with a solution of glucose isomerase for about 5 to about 30 hours. Excess liquid may be removed, and the solid may be washed well with water to remove adhering but mobile enzyme. This completes preparation of an immobilized chemical entity, which in this example is an immobilized enzyme system, viz., glucose isomerase.

An unexpected property of immobilized enzyme systems prepared according to the prior art teachings is that the enzyme system so prepared is variable both in appearance and in initial enzymatic activity. That is to say, support matrices prepared at different times, with different batches of oxide, polyamine and bifunctional reagent, when contacted with identical amounts of enzyme, from a common source, afford immobilized enzyme systems of different appearance and substantially different activity. This results even though the distinct support matrices show no analytical differences on chemical examination.

A surprising discovery of this invention is that drying of the matrix after deposition of the polyamine and before contacting with the bifunctional reagent leads to a support matrix which bonds chemically reactive entities, such as enzymes, with uniform and highly predictable results, thereby eliminating the problems associated with non-reproducible activity. Another discovery is that the aforementioned methods lead to an immobilized enzyme system whose activity is significantly greater than those which have been prepared by prior methods.

The improvement of this invention is practiced as follows. The polyamine is deposited on the core support, for example, an inorganic oxide such as alumina, from an aqueous solution. When impregnation is complete excess liquid is removed by suitable means, such as by decantation, and the polyamine-coated core support is dried. Drying is the critical step of this invention and leads to the improved performed characteristic of the final immobilized enzyme system. Thus, to insure optimum performance, the material must be dried to a final water content from about 1% to about 30% by weight. That is, from about 70% to about 99% by weight of the material after drying is core support and polyamine, and the remainder is water. In a preferred mode the final water content is from about 1% to about 10% by weight, where it is found that improvement in performance is at or near optimum.

Where the matrix is prepared in a batch process drying may be done by the following operations, cited solely for purposes of illustration and not intended as a limitation of this invention. The core support may be placed on a Buchner funnel, and vacuum may be applied until the filter cake begins to crack. This cake may then be spread in a thin film and exposed to the atmosphere for a suitable time, which may vary from about 1 hour to about 25 hours depending upon the air flow and relative humidity. Alternately, drying time may be decreased by heating the material at temperatures up to about 100° C.

The process of drying is well known to those skilled in the art. This invention contemplates the use of any such process, subject to the limitation that it not cause chemical degradation of the polyamine nor physical change in the organic oxide. Examples of suitable processes include drum drying, spray drying, belt drying, etc.

When the support matrix is prepared by a continuous process, the material may be conveniently dried in a fluidized bed. In this method, warm air, or another suitable inert gaseous substance, is introduced to the bottom of a column containing the solid to be dried at a pressure and flow such as to impart fluid transport properties to the solid material. After the bed has been dried to the desired level the gas flow is stopped, and the remaining steps in preparation of the support matrix may be performed in the column.

After the polyamine-coated core support has been dried to the desired water level, preparation of the support matrix is continued as previously described. Thus, the dried polyamine impregnated core support may be contacted with an excess of a bifunctional re-agent which serves to cross-link the amine and which also furnishes a pendant bifunctional group which covalently bonds to the reactive chemical entity. Examples of said bifunctional reagents include glutaraldehyde, terephthalaldehyde, succindialdehyde, and toluenediisocyanate. Contact time may be from about 5 minutes to about 5 hours, with periodic mixing of the phases during this interval. Excess solution is removed, as by decantation, and the solid is washed to remove adhering, but not chemically bound, bifunctional re-agent.

This completes preparation of the improved support matrix. A reactive chemical entity, such as an enzyme, now may be immobilized by suitable means. Using glucose isomerase as an example, immobilization may be performed as previously described.

The examples cited below serve only to illustrate our invention and are not to be construed as limitations thereof.

EXAMPLE 1

In each case glucose isomerase was obtained from Actinoplanes missouriensis and was used as a cell-free extract at a pH of 7-8.

Enzymatic activity was determined by measuring the extent of isomerization of fructose to glucose in a one-hour period under standardized conditions, and using a glucose analyzer to determine the amount of glucose formed.

Gamma-alumina, 25/35 mesh, ABD 0.31, was contacted with an aqueous solution of 4% aminopolystryene, in an amount of 6 ml. per gm. alumina, for one hour at ambient temperature with intermittent shaking. Excess liquid was decanted and solid was washed with an equal volume of water. An aqueous solution of glutaraldehyde, 25% by weight, was added in an amount of 18 ml. per gm. alumina and the mixture was shaken intermittently for an hour. Excess solution was removed by decantation and the solid was washed with water until the washes gave a negative fuchsin aldehyde test.

An exactly equal amount of the same lot of gamma-alumina was coated with aminopolystryene in the same way as described above. However, instead of subsequently being washed with water, the solid was placed on a Buchner funnel and a vacuum was applied until the cake lost its integrity. The cake then was air dried as a thin film by exposure to the atmosphere for about 5 hours. At this time the ABD was in the range of 0.31-0.35, corresponding to 8-9% water by weight. Subsequent cross-linking with glutaraldehyde was performed as above.

Each of the support matrices as prepared was shaken at 4° C. for 18 hours with equal aliquots of a glucose isomerase solution. Liquid was removed by decantation, and mobile but adhering enzyme was removed first by washing with 2M NaCl, then distilled water. The immobilized enzyme system prepared in the usual way showed an activity of 507 units per gm; that prepared by the improved method, which dispensed with the water wash and substituted a drying step prior to cross-linking, showed an activity of 721 units per gram. Hence the improvement of this invention increased activity of the immobilized enzyme system by 42%.

EXAMPLE 2

In this example the polyamine was polyethyleneimine used as a 2.5% aqueous solution in an amount equal to 6 ml. per gm. alumina. Otherwise the procedure was the same as that described in Example 1. Two support matrices were prepared, starting from exactly equal amounts of alumina, differing only in that one was water rinsed prior to cross-linking whereas the other was air dried prior to cross-linking as detailed in the prior example. Each matrix was used to immobilize enzyme from equal aliquots of glucose isomerase preparation in the manner recited previously. Assay of the final preparation showed the water-rinsed system had an activity of 781 units per gm, whereas the air-dried system had an activity of 894 units per gm. Thus, drying to 8-9% water content led to an increase in activity of over 14%.

EXAMPLE 3

In these experiments alumina was 60/80 mesh, but otherwise these experiments were performed as described in Example 2. The water-rinsed preparation showed an activity of 1794 units per gm., whereas the dried preparation showed an activity of 2051 units per gm., an increase of over 14% in activity.

EXAMPLE 4

This example shows the activity of the immobilized enzyme system varies with the degree of drying after alumina has been coated with polyethyleneimine. Following the general procedure described in Example 2 one portion was air-dried to 10% by weight water, and an exactly equal portion was dried to 7% by weight water. Subsequent cross-linking and glucose isomerase immobilization gave systems of activity 1566 and 1859 units per gm., respectively. This example shows how the degree of drying effects the activity of the immobilized enzyme system, and shows that drying to a 7% water content increases activity by 18% compared to drying to 10% water content.

EXAMPLE 5

In this example, various batches of glucose isomerase were immobilized by the procedure of Example 2, where the matrix was dried to about 7% water content after polyethyleneimine impregnation. Preparation of the immobilized enzyme systems spanned an interval of several weeks. The activities observed, in units per gram of immobilized enzyme system, were: 2026, 1831, 1873, 1918, 1873, 1799, 1973, 2164, 1921, 2030, 2081, 1794, 2216, 1960, 1895. The average activity was 1957 units per gram, with a standard deviation of 6%. (126 units)

These data show the excellent reproducibility in immobilized enzyme system preparation afforded by drying the polyamine-impregnated support before cross linking.

What is claimed is:

1. A method for preparing a support matrix for immobilization of an enzyme which comprises:
  (a) depositing a polyamine binding layer selected from the group consisting of aminopolystyrene and polyethyleneimine on an alumina support in an aqueous solution;
  (b) removing excess polyamine from said alumina support;
  (c) drying said alumina support of step (b) prior to contacting said alumina support with glutaraldehyde in step (d) to provide a final water content of from about 1% to about 30% by weight of said alumina support;
  (d) contacting said dried alumina support of step (c) with a solution containing an excess of glutaraldehyde to provide crosslinkage between said glutaraldehyde and said polyamine binding layer; and (e) recovering the resultant support matrix for immobilization of said enzyme.

2. The method of claim 1 wherein said drying of said matrix is continued until the water content of said matrix ranges from about 1% to about 10% by weight of the weight of said alumina support.

3. The method of claim 1 wherein said enzyme is selected from the group consisting of glucose isomerase, glucoamylase, cholesteroloxidase, alcohol dehydrogenase, amino acid oxidase, arginse, asparaginase, catalase, chymotrypsin, cellulase, collagenase, deoxyribonuclease, ficin, histidase, lactase, peroxidase, lysozyme, gamma amylase, papain, rennin, ribonuclease and urease.

* * * * *